(12) United States Patent
Vasan et al.

(10) Patent No.: US 10,537,402 B2
(45) Date of Patent: Jan. 21, 2020

(54) SURGICAL CLEANING TOOL, SYSTEM, AND METHOD

(71) Applicant: The Board of Regents of the University of Oklahoma, Norman, OK (US)

(72) Inventors: Nilesh Vasan, Oklahoma City, OK (US); Michael Petri, Richardson, TX (US); Andrew Stewart, Edmond, OK (US); Patrick Stevens, Norman, OK (US); Rannyu Ngoran, Norman, OK (US); Jonathan Schick, Duncan, OK (US); Derrick Jones, Norman, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

(21) Appl. No.: 15/529,416

(22) PCT Filed: Nov. 24, 2015

(86) PCT No.: PCT/US2015/062493
§ 371 (c)(1),
(2) Date: May 24, 2017

(87) PCT Pub. No.: WO2016/086028
PCT Pub. Date: Jun. 2, 2016

(65) Prior Publication Data
US 2017/0354476 A1 Dec. 14, 2017

Related U.S. Application Data

(60) Provisional application No. 62/083,740, filed on Nov. 24, 2014.

(51) Int. Cl.
*A61B 90/70* (2016.01)
*B08B 1/00* (2006.01)

(52) U.S. Cl.
CPC .............. *A61B 90/70* (2016.02); *B08B 1/002* (2013.01); *B08B 1/006* (2013.01)

(58) Field of Classification Search
CPC ... A61B 90/70; A61B 1/126; A61B 2090/701; A61B 1/122
See application file for complete search history.

(56) References Cited

U.S. PATENT DOCUMENTS 5,423,814 A   6/1995  Zhu et al.
5,456,681 A   10/1995 Hajjar
(Continued)

OTHER PUBLICATIONS

International Search Report and Written Opinion; International Application No. PCT/US2015/062493; dated Mar. 1, 2016; 9 pages.

*Primary Examiner* — Mikhail Kornakov
*Assistant Examiner* — Natasha N Campbell
(74) *Attorney, Agent, or Firm* — Hall Estill Law Firm

(57) ABSTRACT

A surgical cleaning tool and method of cleaning a surgical tool. The surgical cleaning tool includes a shaft, a handle and an end portion. The shaft has a distal end and a proximal end. The handle is attached to the distal end of the shaft The end portion is connected to the proximal end of the shaft, wherein the end portion has an outer surface, an inner cavity, an inner surface, at least one cleaning element connected to at least a portion of the inner surface, and an opening in a wall portion of the end portion, wherein the opening allows access to the cleaning element in the inner cavity of the end portion.

13 Claims, 18 Drawing Sheets

(56) References Cited

U.S. PATENT DOCUMENTS

| | | | |
|---|---|---|---|
| 5,658,273 | A | 8/1997 | Long |
| 6,309,397 | B1 | 10/2001 | Julian et al. |
| 6,770,081 | B1 | 8/2004 | Cooper et al. |
| 7,125,403 | B2 | 10/2006 | Julian et al. |
| 7,347,856 | B2 | 3/2008 | Wittenberger et al. |
| 7,772,599 | B2 | 8/2010 | Udagawa |
| 8,182,476 | B2 | 5/2012 | Julian et al. |
| 8,551,116 | B2 | 10/2013 | Julian et al. |
| 2014/0018824 | A1 | 1/2014 | Julian et al. |
| 2014/0215736 | A1* | 8/2014 | Gomez ............... A61B 1/00154 15/104.05 |
| 2014/0263541 | A1* | 9/2014 | Leimbach ............... A61B 34/30 227/175.2 |
| 2016/0066913 | A1* | 3/2016 | Swayze ................ A61B 17/072 227/176.1 |

\* cited by examiner

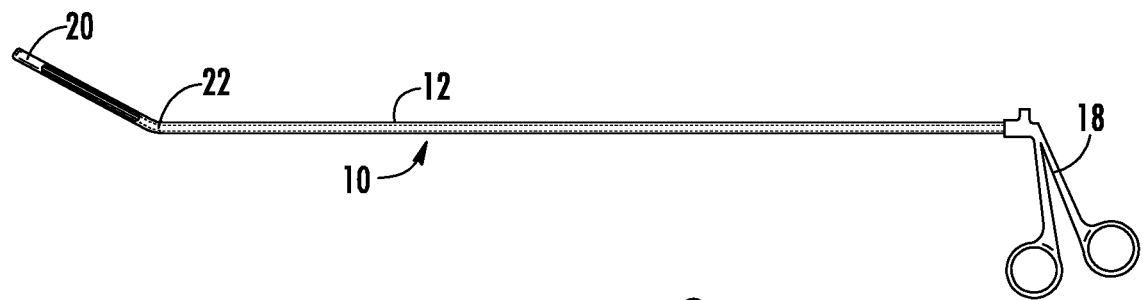
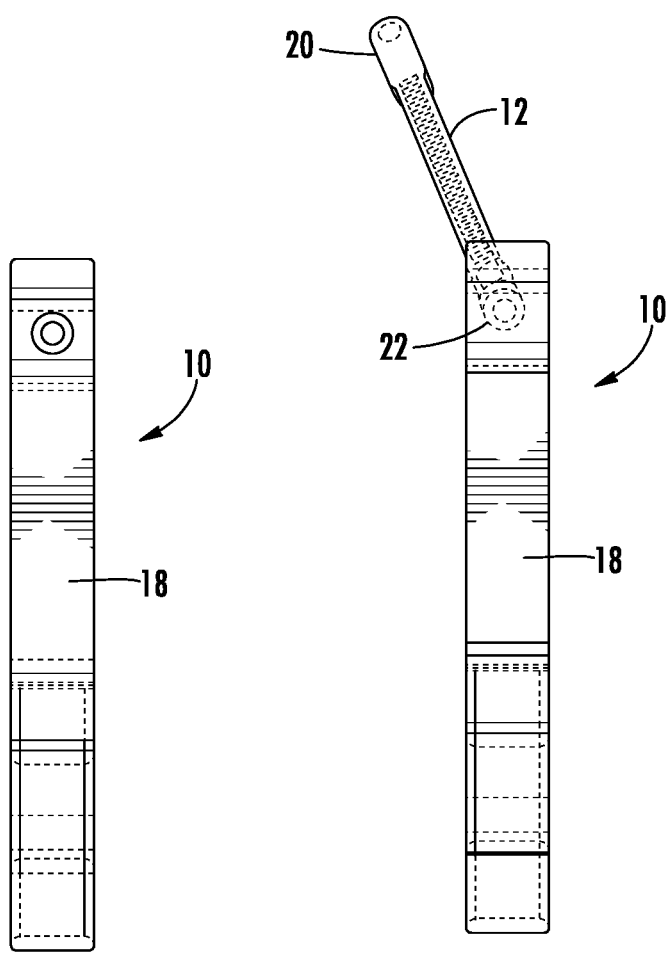
FIG. 2
FIG. 3  FIG. 4

SURGICAL CLEANING TOOL, SYSTEM, AND METHOD

CROSS-REFERENCE TO RELATED APPLICATIONS

The present application is a national stage application of a PCT application having International Application No. PCT/US2015/062493, filed Nov. 24, 2015, which claims priority to U.S. Provisional Application having U.S. Ser. No. 62/083,740, filed Nov. 24, 2014, which claims the benefit under 35 U.S.C. 119(e). The disclosure of which is hereby expressly incorporated herein by reference.

BACKGROUND

Surgeons who use electro-cautery tools (e.g., "cautery tools," "surgical tools," "surgical instruments," or "robotic tools,") and/or laser tools within body cavities cause charring of patient tissue. The charred tissue builds up on the cautery tool surface and inhibits the effectiveness of the cautery tool. Currently, proper cleaning of these surgical tools requires removal of the surgical tool from the patient's body to be cleaned manually, externally, by a surgical assistant. This cleaning process may be needed as often as every 5 to 10 minutes, depending on the surgery, and each tool removal step may consume as much as 1 to 2 minutes. Established practice for cleaning of the cautery tools dictates the use of cloth, gauze, sponge or abrasive (e.g., polyurethane) pads to remove charred tissue from the cautery tool and then reattaching the cautery tool to the robotic surgical system and reintroducing the cautery tool to the internal surgical site through an opening into the body cavity.

In an effort to avoid the time consumption required to clean surgical tools with this established practice, many surgeons scrape their surgical tools together at the surgical site (internally) to remove charred tissue from their instruments. Cupspoon or grasping forceps, a commonly used laparoscopic accessory tool manipulated by the surgical assistant, are also used for cleaning surgical instruments at the surgical site, but are only effective at removing large chunks of tissue. Therefore, cupspoon forceps do not resolve the charred tissue buildup problem. Furthermore, tool scraping is a dangerous practice, as contacting the tools in this manner can lead to accidental electrical arcing or the forceful release of tension from two tools being pressed together, leading to the potential for puncture wounds. Tool scraping also dulls bladed tools, leading to less effective instruments and shortened usable lifespan. New tools and methods to alleviate and resolve these problems would be desirable and it is to such a solution that the presently disclosed inventive concepts are directed.

BRIEF DESCRIPTION OF THE DRAWINGS

Several embodiments of the present disclosure are hereby illustrated in the appended drawings. It is to be noted however, that the appended drawings only illustrate several typical embodiments and are therefore not intended to be considered limiting of the scope of the presently disclosed inventive concepts.

FIG. 2 is a side view of the cleaning tool of FIG. 1 in an angled position.

FIG. 3 is an end view of the cleaning tool of FIG. 1 in a straight position.

FIG. 4 is an end view of the cleaning tool in FIG. 1 in an angled position.

DETAILED DESCRIPTION

The presently disclosed inventive concepts include a surgical accessory tool, referred to herein by the term IvTEC ("In-vivo Tool for Electrocautery Cleaning") and also referred to herein as an "accessory tool," "surgical accessory," "cleaning tool," or "surgical cleaning tool." The cleaning tool provides surgeons, particularly those working with robotic surgical systems, a way to clean surgical tools, including but not limited to those with electrocautery function, laser-cautery function, or other energy emitting capabilities, at the surgical site (inside the patient) without having to remove the surgical tool from the (intra-body) surgical site to be cleaned externally. As mentioned, this cleaning tool is particularly applicable to robotic surgeries, but has applications in other surgeries including, but not limited to, general laparoscopic surgeries, open surgeries, and combined open, robotic, and/or laparoscopic surgeries. In each, also as mentioned, this cleaning tool has utility in cleaning electrocautery tools, tools with laser functions, and any other surgical instruments that emit thermal energy against tissue.

The present application claims the benefit under 35 U.S.C. § 119(e) of U.S. Provisional Application Ser. No. 62/083,740, filed Nov. 24, 2014, entitled "SURGICAL CLEANING TOOL, SYSTEM AND METHOD," which is hereby expressly incorporated herein in its entirety.

Figure 1:
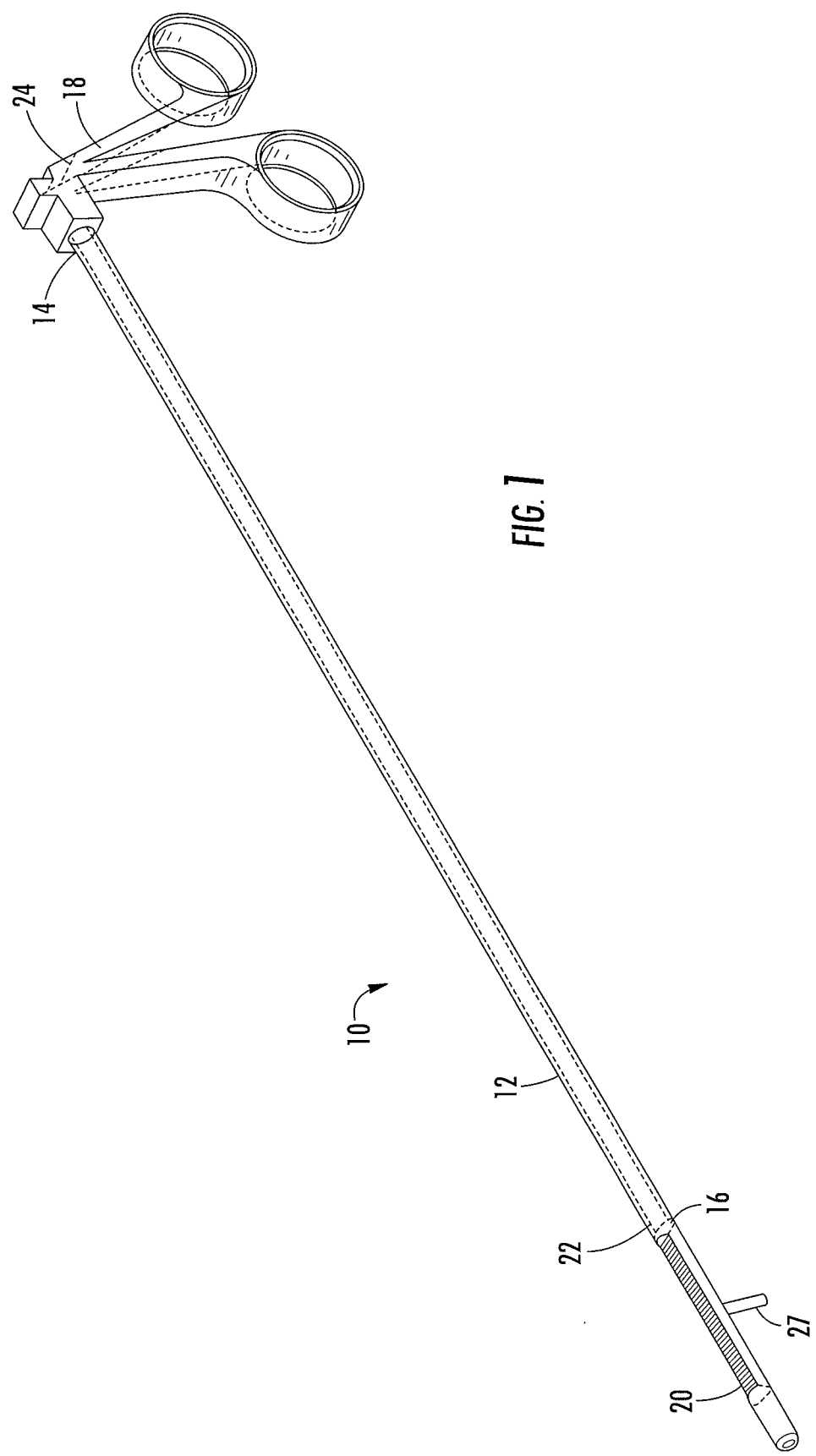
FIG. 1 is an isometric view of one embodiment of a cleaning tool constructed in accordance with the present disclosure.
Figure 5:
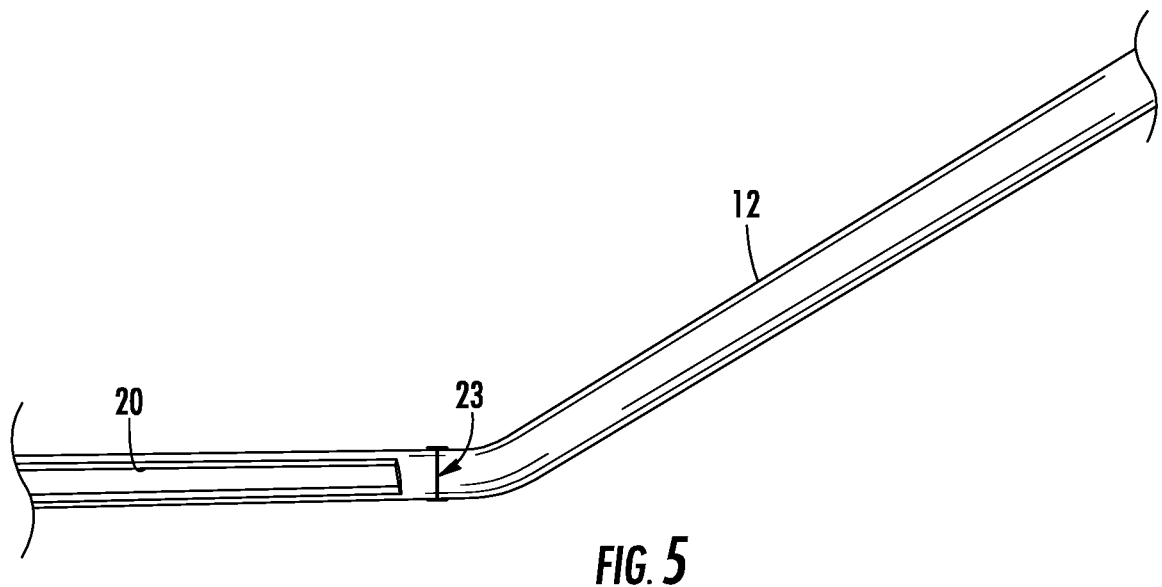
FIG. 5 is a side view of an end portion of the cleaning tool of FIG. 1 in the angled position.
Figure 6:
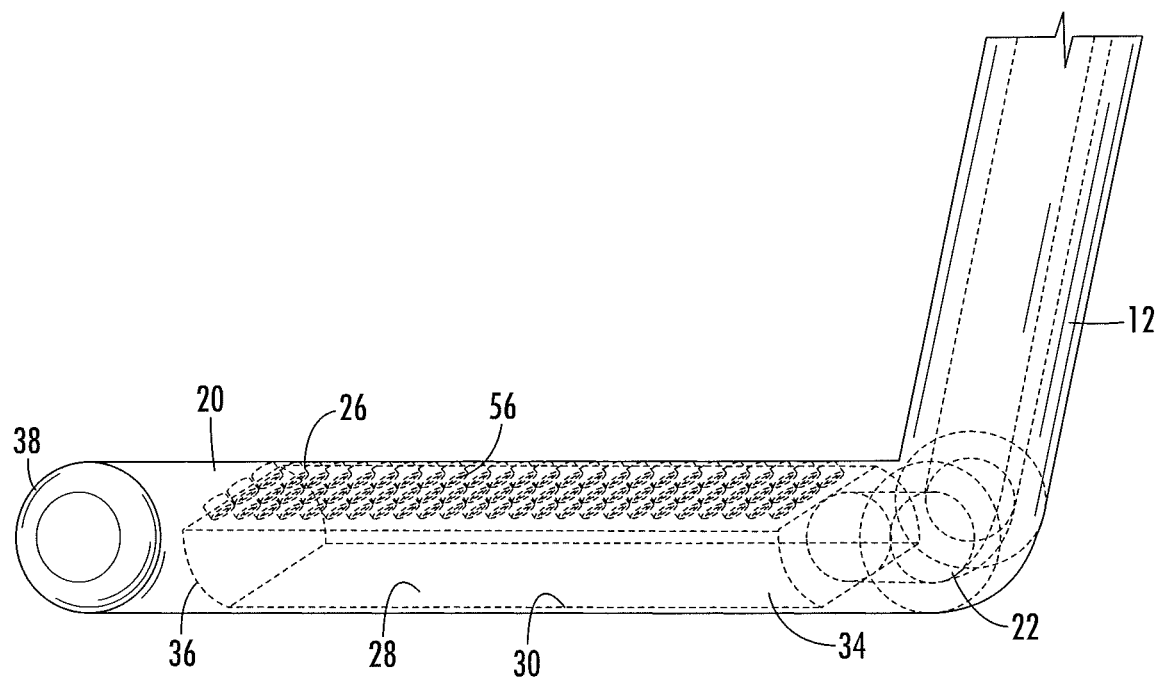
FIG. 6 is a cut-away view of the end portion of the cleaning tool of FIG. 5.
Figure 7:
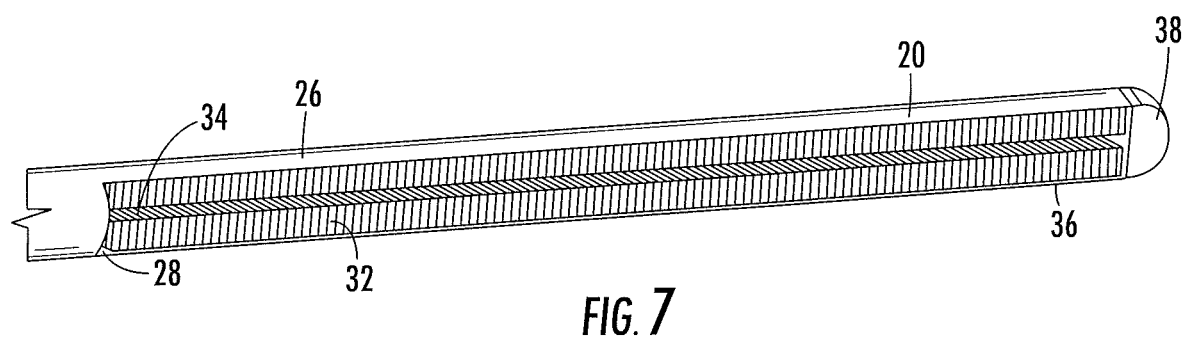
FIG. 7 is a side view of the end portion of the cleaning tool of FIG. 1.
Figure 8:
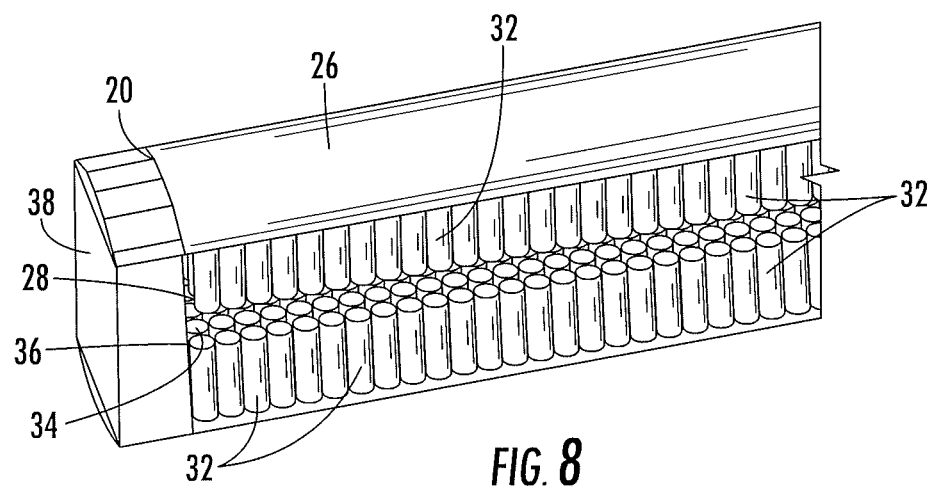
FIG. 8 is a close-up side view of the end portion of the cleaning tool of FIG. 7.
Figure 9:
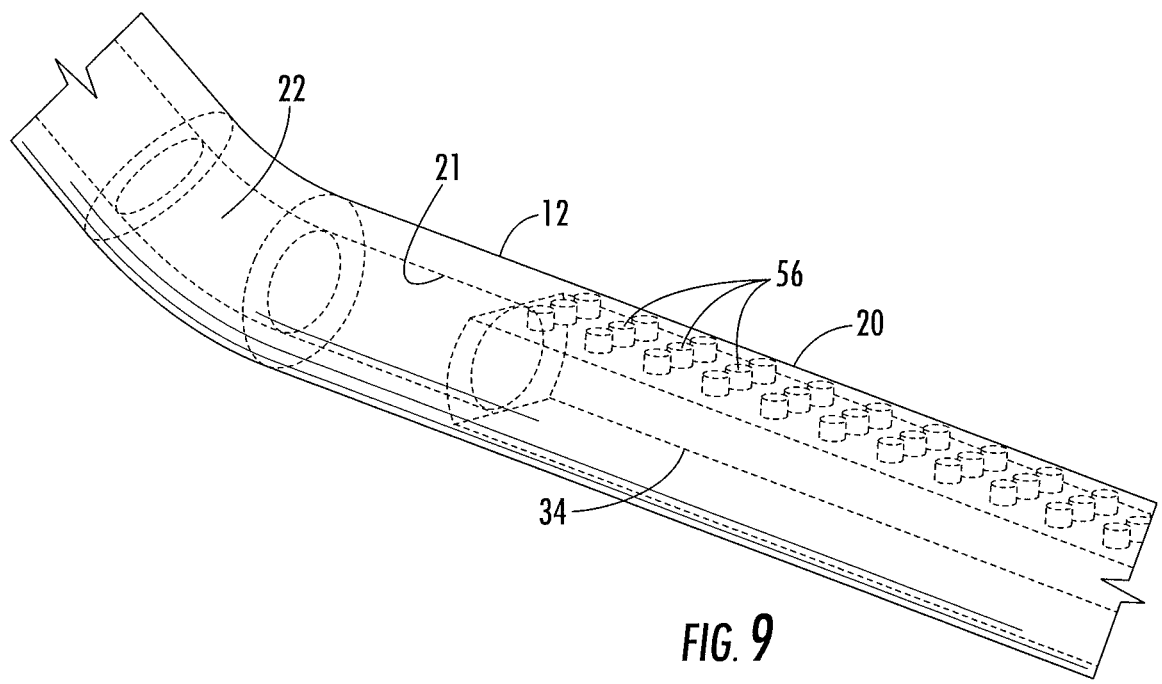
FIG. 9 is a transparent view of an end portion of another embodiment of a cleaning tool constructed in accordance with the present disclosure.

The cleaning tool disclosed herein enables in-vivo cleaning of surgical tools and combines the effectiveness of the established (external) cleaning practice with the convenience and time-savings of an internal method. Referring now to the drawings, and more particularly to FIG. 1, shown therein is one non-limiting embodiment of a cleaning tool 10 constructed in accordance with the inventive concepts disclosed and claimed herein. The cleaning tool 10 includes a shaft 12 having a distal end 14 and a proximal end 16, a handle 18 graspable by a user (not shown) attached to the distal end 14 of the shaft 12, and an end portion 20 connected to the proximal end 16 of the shaft 12.

Components of the cleaning tool 10 can be made of materials including, but not limited to metal, metal alloys, plastic and/or polymers, a coated metal, a ceramic material, or a rigid or semi-flexible plastic material, such as, but not limited to, a high density polyethylene (HDPE), acrylonitrile butadiene styrene (ABS), or other synthetic, carbon-based polymer or combination thereof. Some components may be autoclaved and/or sterilized. Components may also be constructed of sterile materials.

The shaft 12 may be solid or hollow or partially hollow and may be constructed of similar materials as disclosed herein, such as, but not limited to, rigid or semi-flexible plastic materials, metals, or medical grade coated or uncoated metals, such as stainless steel (S.S.) 440C or aluminum or combinations thereof. Similarly, the handle 18 can be constructed of a material such as described herein. The shaft 12 may have a separate tube or conduit 21 longitudinally attached thereto or externally integral thereto for supplying a saline solution to the end portion 20. The shaft 12 attaches the end portion 20 to the handle 18. The handle 18 of the cleaning tool 10 is similar to that used to manipulate existing laparoscopic tools known in the art.

The end portion 20 may be connected to the shaft 12 by a hinge mechanism 22 (also referred to herein as an angling mechanism) which is adjustable in two or three dimensions, as shown in FIGS. 2-6. The hinge mechanism 22 is positioned between the end portion 20 and the proximal end 16 of the shaft 12. A trigger mechanism 24 is positioned in the handle 18 that enables actuation of movement of the hinge mechanism 22 by the user to effect a change in an angle of the end portion 20 in relation to the shaft 12. The angle of the end effector 20 in relation to the shaft 12 may be changed from 0° to 90° or more to allow better surgical tool access to the cleaning surface of the end effector 20. In certain embodiments, the change of angle of the angling mechanism is controlled with a trigger or button 25 that the assistant controls (See FIG. 1). The trigger or button 25 may control the action of the trigger mechanism 24 via one or more narrow metal rods, cables, wires, string, springs, and/or pulleys, or any combination of these or similar, small, mechanical structures. The action of the trigger 25 is translated to the angling motion of the angling mechanism 22 for changing the orientation of the end effector 20 in two dimensions or three dimensions. In certain embodiments, the trigger 25 angles the end effector 20 in one of two directions. These two directions are 180° offset from each other, i.e., the end effector 20 can angle left or right. Multidirectional functionality (more than 2 directions of motion) and other degree offsets (45°, 60°, or 120°, for instance) may also be included. A locking mechanism (not shown) may optionally be present to allow the end effector 20 to remain stationary and stable in any fraction of its range after the trigger 25 has moved the end effector 20 to the desired angle. The hinge (angling) mechanism 22 may comprise one or more 'joint like' hinges. The hinge mechanism 22 may also allow for a "rotational" ('wristed') movement similar to that of the Da Vinci robotic surgical arms. The external diameter 23 of the shaft 12 of the cleaning tool 10 is minimized in certain embodiments so that it can be inserted into a 5 mm diameter (or other sizes as indicated below) laparoscopic port and safely introduced to the surgical site.

The cleaning tool 10 may also have an element 27, such as a small tab, flange, extension, or handle attached to the end portion 20 (FIG. 1) or elsewhere along the shaft 12 that is graspable by the surgeon's robotic tools, enabling the surgeon to manipulate and reposition the cleaning tool 10 as desired.

Referring to FIGS. 1, 2, 3, and 7-9, the end portion 20 (also referred to herein as an end effector) has an outer surface 26, an inner cavity 28, an inner surface 30, at least one cleaning element 32 and an opening 34 in a wall portion 36 of the end portion 20. The at least one cleaning element 32 is connected to at least a portion of the inner surface 30. The end portion 20 is a hollow shell constructed of a material such as, but not limited to, a coated metal, a ceramic material, or a rigid or semi-flexible plastic material, such as, but not limited to, a high density polyethylene (HDPE), acrylonitrile butadiene styrene (ABS), or other synthetic, carbon-based polymer or combination thereof. The opening 34 is for receiving a surgical tool.

The tip 38 of the end portion 20 of the cleaning tool 10 can be rounded so as to avoid the potential for puncture wounds and can be easily and quickly removed from a port at any time. The cleaning tool 10 has been designed to be removable quickly without the potential of a "barbed hook effect," so that removal of the cleaning tool 10 through the laparoscopic port is not inhibited.

As noted, the end portion 20 of the cleaning tool 10 has a cleaning element 32 (also referred to herein as a cleaning surface) into which the surgical tool is inserted wherein the surgical tool is rubbed, scraped, scoured, or otherwise moved against the cleaning element 32 to cause removal of charred tissue from the surgical tool using friction. The cleaning element 32 may be constructed of traditional materials used for cleaning, such as, but not limited to, bristles, protuberances, brushes, pads, open- or closed-cell foam, natural or synthetic sponge, porous inert substances, cotton, fabrics, natural or synthetic materials, polymeric materials such as nylon or polyurethane, flexible materials, and/or rigid materials. The cleaning element 32 can be made of a single material or a combination of materials from classes such as polyurethane, nylon, polyethylene, or other synthetic, carbon-based polymers, as well as other materials described elsewhere herein. The cleaning element 32 of the end portion 20 may be attached to the inner surface 30 of the end portion 20 through chemical adhesion or physical attachment, or any other suitable means.

Generally, laparoscopic surgical port dimensions range from 3 mm to 12 mm, so the external diameter of the cleaning tool shaft and end effector will be less than 12 mm, for example in a range of from about 3 mm to 7 mm. In one embodiment the external diameter of the shaft and end effector is 5 mm. In certain non-limiting embodiments, the end effector has a length in a range of about 2 mm to about 100 mm, or for example a range of about 20 mm to about 50 mm. The entire cleaning tool from the tip of the end effector to the handle will generally have, but is not limited to, a length in a range of from about 150 mm to about 1000 mm, for example in a range of from about 300 mm to about 600 mm. In one embodiment, the cleaning tool has a length in a range of about 400 mm to about 500 mm. The handle has dimensions which are about the same as handles used on other commonly used laparoscopic instruments.

Another benefit of the cleaning tool disclosed herein, in certain embodiments, is the ability to use it to cool a surgical tool so that the risk of thermal injury to tissues or organs by a hot electro-cautery tool may be reduced. In certain embodiments, cool saline solution can be provided through or adjacent the shaft and applied onto, through or into the cleaning element of the cleaning tool (as explained below) so that heat energy of the hot electro-cautery tool may be quickly removed/dissipated as it is cleaned. The cleaning tool end effector could also be soaked in saline prior to insertion and the retained fluid would also aid in cooling of the instrument. The cooling saline is also used to help prevent thermal distortion of the materials of the cleaning element of the cleaning tool. By taking advantage of the relatively high heat capacity of water, thermal energy may be rapidly removed from the surgical cautery tool, thus protecting both the patient and the cleaning element material.

Method of Cleaning Tool Insertion/Assistant Interaction

In use, a surgical assistant manually inserts the cleaning tool 10 through a laparoscopic port or through an open cavity and maneuvers the accessory tool to the surgical site of the patient. In general, the cleaning tool 10 is not maneuvered by, manipulated by, or coupled to other surgical instruments, such as a Da Vinci Surgical System™ forceps. In certain embodiments, however, the cleaning tool 10 may also have a small "tab," "flange," "extension", or "handle" attached to a portion thereof, for example, along the shaft or on the effector end that is graspable by the surgeon's surgical tools, enabling the surgeon to manipulate and reposition the cleaning tool as desired. The surgical assistant controls the cleaning tool 10 externally by using the handle (FIG. 1) which remains outside of the patient's body.

Method of Use of Cleaning Tool to Clean Surgical Tool

Figure 10:
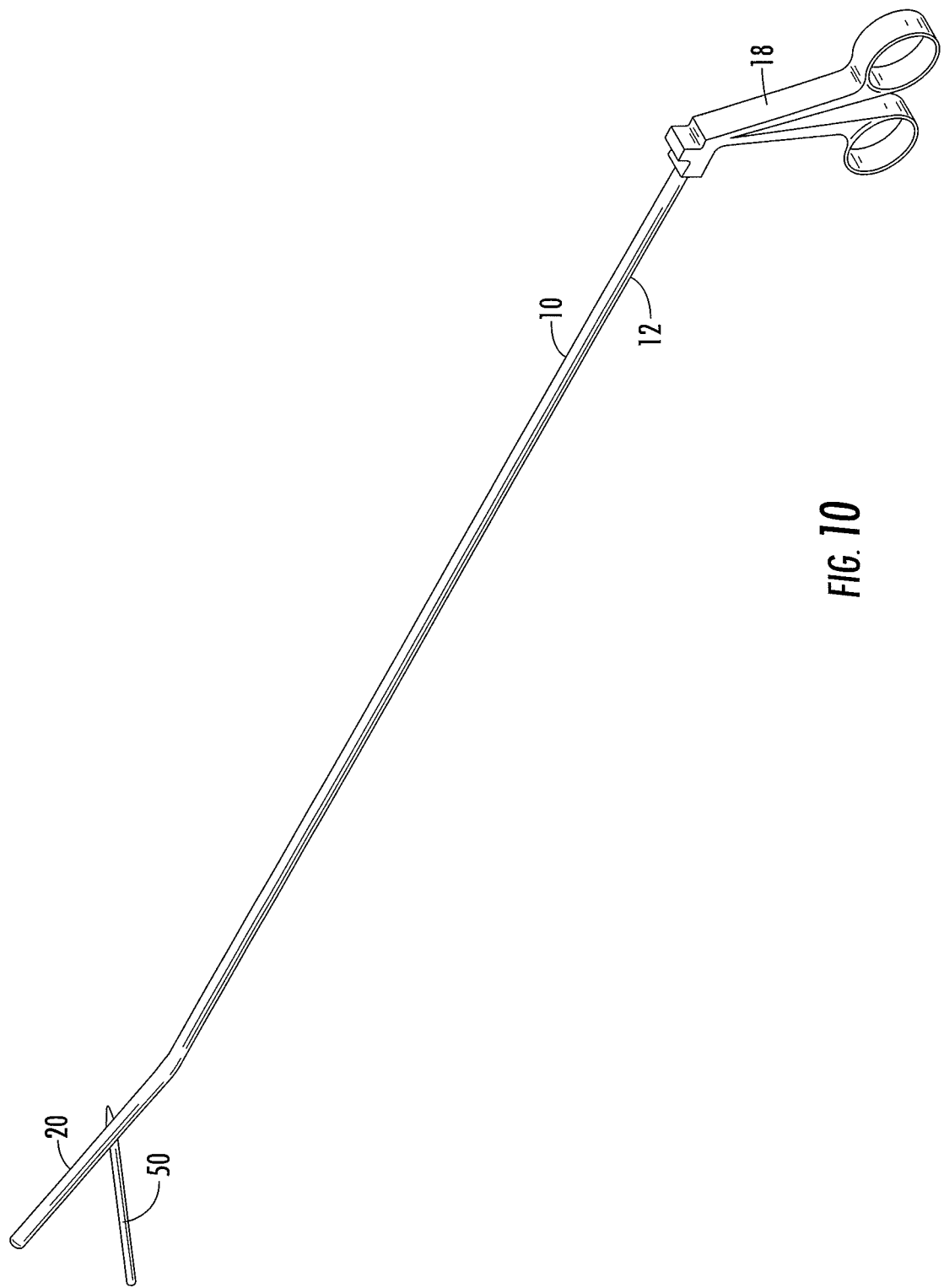
FIG. 10 is a perspective view showing the interaction between the cleaning tool of FIG. 1 and a surgical tool.
Figure 11:
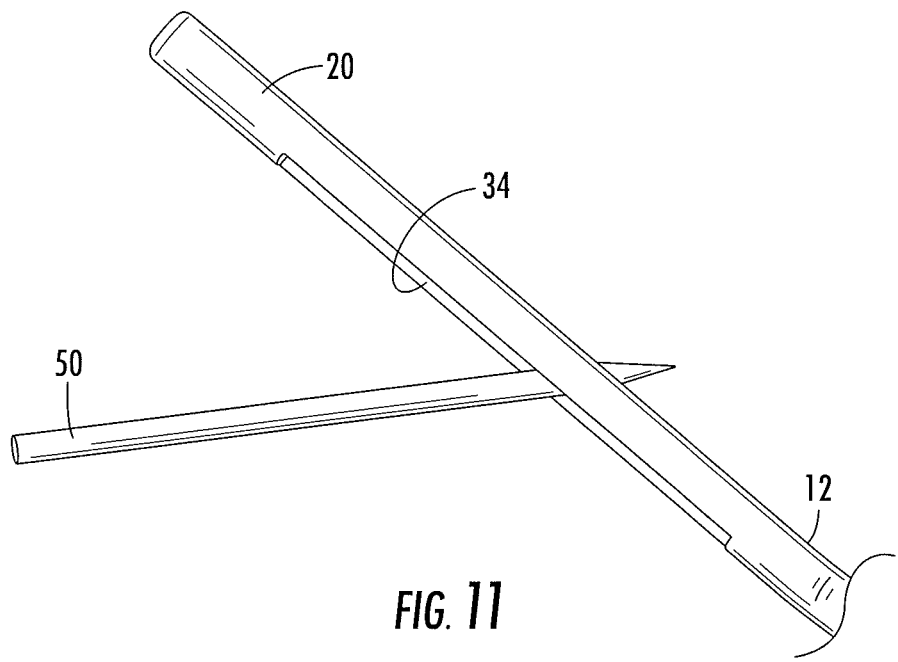
FIG. 11 is a top view of an end portion of the cleaning tool and surgical of FIG. 10.
Figure 12:
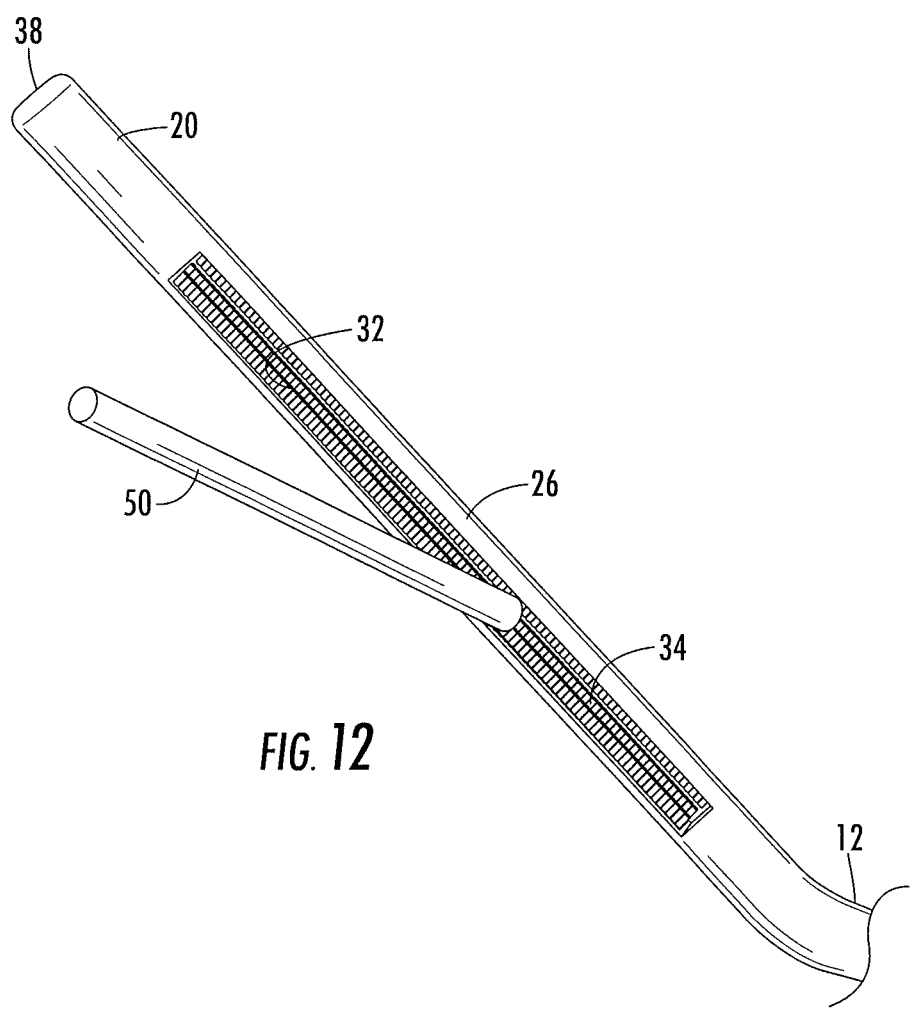
FIG. 12 is a side view of the end portion of the cleaning tool interacting with the surgical tool of FIG. 10.

Referring to FIGS. 10-12, a surgical tool 50 is utilized with the cleaning tool 10 as described herein. During a surgical procedure, the surgical tool 50 has been inserted by a surgeon into a body cavity or internal site of a patient. After use, charred tissue accumulates on the surgical tool 50. The surgeon partially or completely inserts the surgical tool 50 into the opening 34 of the end portion 20 having the cleaning element 32, wherein the tool 50 is rubbed, scraped, and/or scoured by or against the cleaning element 32, e.g., bristles, to remove charred tissue from the surgical tool 50. The end portion 20 may also have one or more water jets (not shown) to aid in the removal of the charred tissue. The surgical tool 50 can be inserted into the end portion 20 of the cleaning tool 10 from several different angles, including either of the two open sides 34a and 34b, the end of the tool 10 (should an end cap 52 be removed from the cleaning tool 10), other entry ports (should more than 2 lengthwise openings be included in the design), or an opening orthogonal to the plane of insertion (an opening facing "backward" toward the laparoscopic port through which the cleaning tool may be inserted). The surgical tool 50 is manipulated by surgeon to contact the cleaning element 32 of the cleaning tool 10 as described above to apply force to the surgical tool 50 and charred tissue thereon to achieve desired tissue removal from surgical tool 50. The cleaning tool 10 remains stationary, unless angling of end portion 20 or repositioning of the tool 10 is desired by the surgeon, at which point the surgical assistant manipulating the cleaning tool 10 controls the angle with handle 18 or positional change by physically moving or rotating the tool 10. Primary control and orientation of the cleaning tool 10 is done externally by the assistant. These movements are independent of the surgeon or robotic surgical system. The cleaning tool 10 may be removed from (or inserted into) the patient at any time. Positioning of the end portion 20 of the cleaning tool 10 is also dependent upon how far the tool 10 is inserted into the patient, the same as with any laparoscopic accessory tool used by surgical assistants.

As noted above, the cleaning tool 10 may also have the element 27, such as small tab, flange, extension, or handle attached to the end effector 20 or elsewhere along the shaft 12 that is graspable by the surgeon's robotic tools, enabling the surgeon to manipulate and reposition the cleaning tool 10 as desired. The supports or cap 52 of the end effector tip 38 may also be used for this surgeon-guided function. This feature of enabling the surgeon to guide the tool 10 increases the versatility of the cleaning tool 10 and enables the tool 10 to be more easily and more efficiently positioned near the surgical site for easier access to the cleaning element 32 in certain situations.

As noted above, referring to FIG. 9, a cooling effect may be performed during the cleaning operation through the use of cool saline solution, particularly when intense surgical tool power settings, and therefore high temperatures, are involved. In certain embodiments the cool saline solution is provided through the conduit /tube 21 within the shaft 12 of the cleaning tool 10 (or alternately via a tube attached to the outside of the shaft) and supplied to cleaning element 32 through small holes 56 on the inner surface 30 of the end effector 20 where the cleaning element 32 is connected to the inner surface 30.

Figure 13:
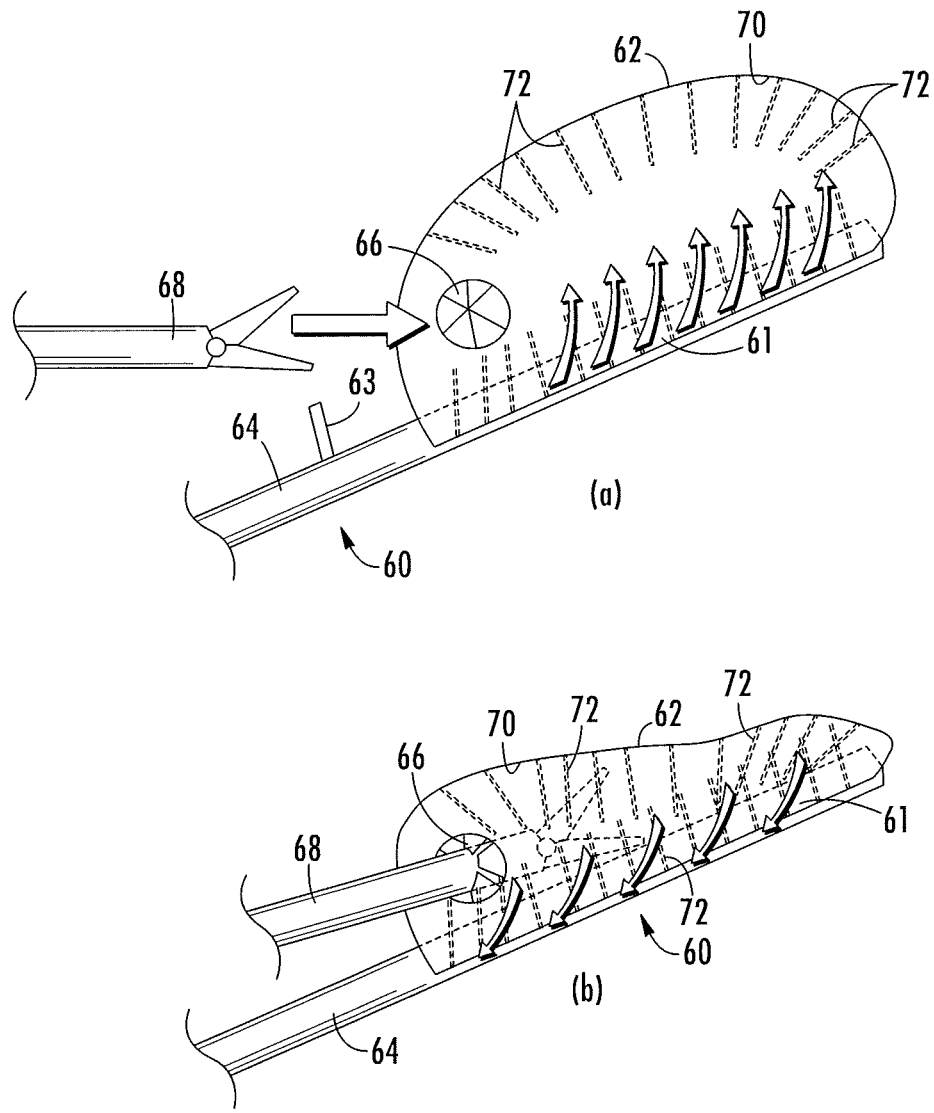
FIG. 13a is a perspective view and another embodiment of a cleaning tool having an end portion in an inflated position.
FIG. 13b is a perspective view and another embodiment of a cleaning tool having an end portion in a deflated position.

Referring now to FIGS. 13a and 13b, shown therein is another embodiment of a cleaning tool 60 similar to the cleaning tool 10 except that a cleaning element 61 of the cleaning tool 60 includes an inflatable balloon 62 moveable between an inflated position (FIG. 13a) and a deflated position (FIG. 13b). Various mechanisms known for inflating and deflating an object may be utilized for inflating and deflating the balloon 62 with air and may be positioned in the shaft 64 of the cleaning tool 60. The balloon 62 has a single, one-way valve 66 for receiving a tool 68, such as a cauterizing tool, and an inner surface 70 having bristles 72. In use, for example, the cauterizing tool 68 having charred material is inserted through the valve 66 of the balloon 62 while in the inflated position. A suction mechanism (not shown) is triggered to collapse the balloon 62 into the deflated position. The bristles 72 are used to scrap off the charred material on the cauterizing tool 68. The charred tissue/material removed from the tool 66 is contained inside of the balloon 62. The cleaning tool 60 similar to cleaning tool 10 may also have an element 63, such as a small tab, flange, extension, or handle attached along the shaft 64 that is graspable by the surgeon's robotic tools, enabling the surgeon to manipulate and reposition the cleaning tool 60 as desired.

Figure 14:
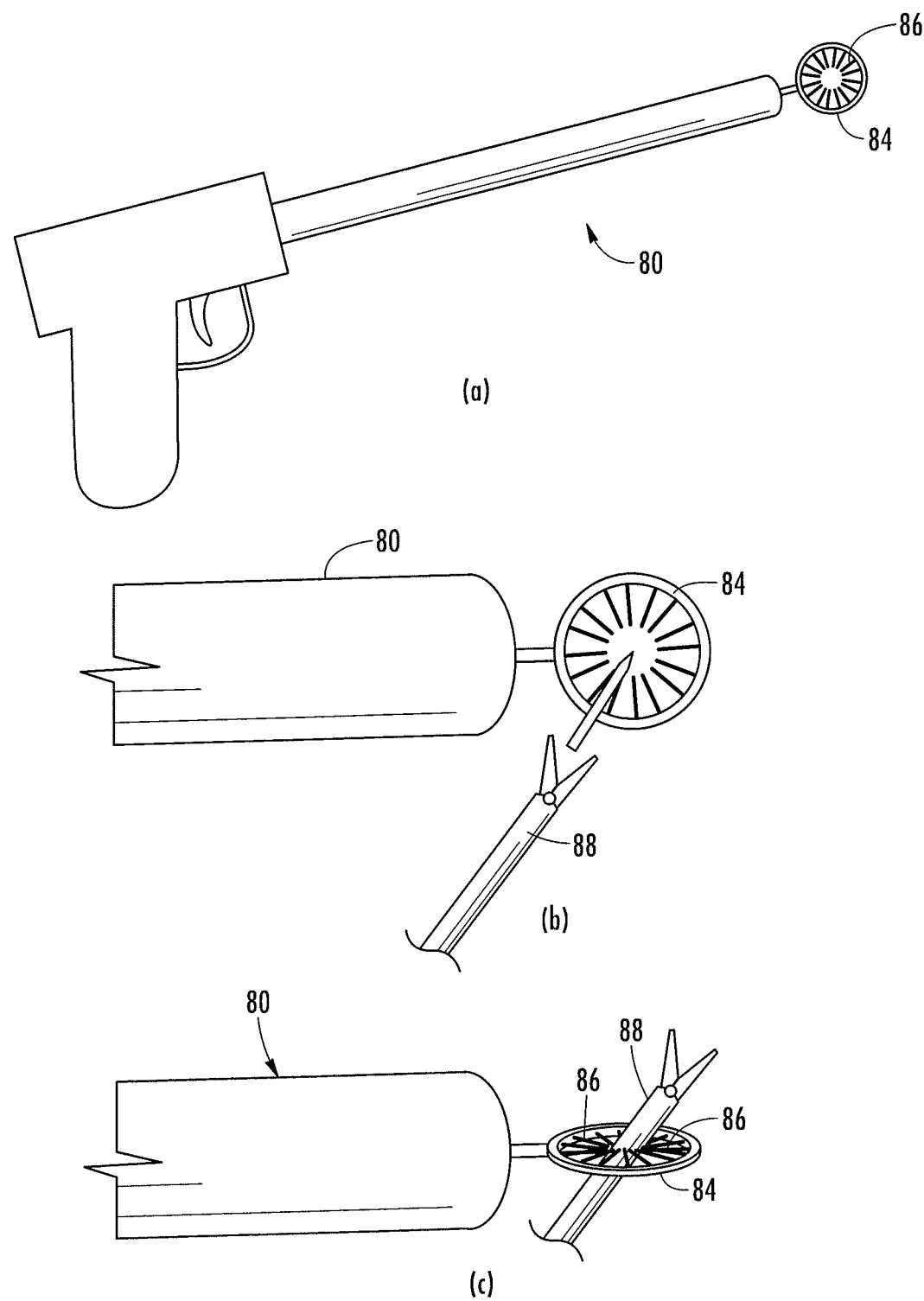
FIG. 14a is a side view of another embodiment of a cleaning tool having a cleaning element with a collapsible ring.
FIG. 14b is a side view of the cleaning element of the cleaning tool of FIG. 14 in an open position.
FIG. 14c is a side view of the cleaning element of the cleaning tool of FIG. 14 in a closed position.

Referring now to FIGS. 14a-14c, shown therein is another embodiment of a cleaning tool 80 similar to the cleaning tool 10 except that a cleaning element 82 of the cleaning tool 80 comprises a collapsible ring 84 having bristles 86. The collapsible ring 84 is movable between an open position (FIG. 14b) and a collapsed position (FIG. 14c). In use, a surgical tool 88 is inserted into the open ring 84 of bristles 86 in the open position. The ring 84 is compressed (e.g., through trigger or other mechanism action) into the collapsed position in order for the bristles 86 to come into contact with the tool 88 so as to remove any charred tissue from the tool 88, as discussed herein.

Figure 15:
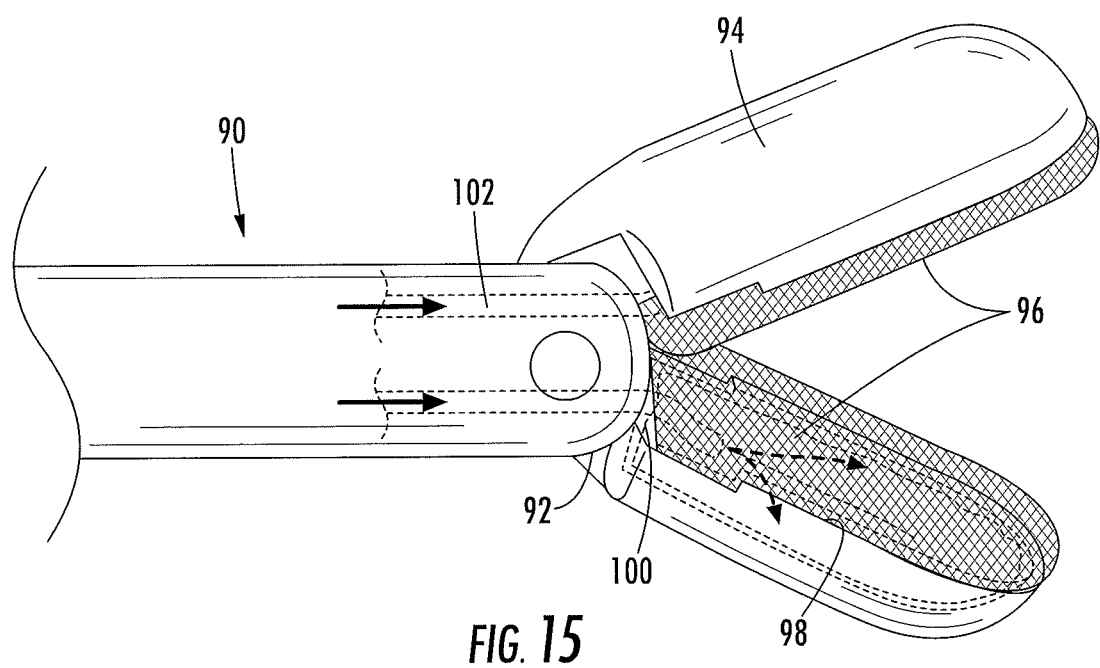
FIG. 15 is a perspective view of another embodiment of a cleaning tool having an end portion with modified forceps.

Referring to FIG. 15, shown therein is another embodiment of a cleaning tool 90 similar to the cleaning tool 10 except that a cleaning element 92 includes modified forceps 94 movable between an open position and closed position. The modified forceps 94 are similar to cupspoon forceps, a common laparoscopic tool. However, the forceps 94 includes bristles or an abrasive pad 96 on the inside surface 98 of jaws 100 of the forceps 94. In use, a surgical tool, such as a cautery tool, (not shown) is positioned on the inside surface 98 of the jaws 100 in the open position. This would allow the surgeon's assistant to clamp down and close the jaws 100 on the surgical tool and use pressure and friction to remove charred tissue from the tool. A cooling system 102 may be provided that would supply water, or possibly saline, to the mouth of the forceps 94. This allows for a better cleaning capability as well as cooling down the tool and preventing the bristles or pads 96 of the forceps 94 from being damaged from the heat of the tool.

Figure 16:
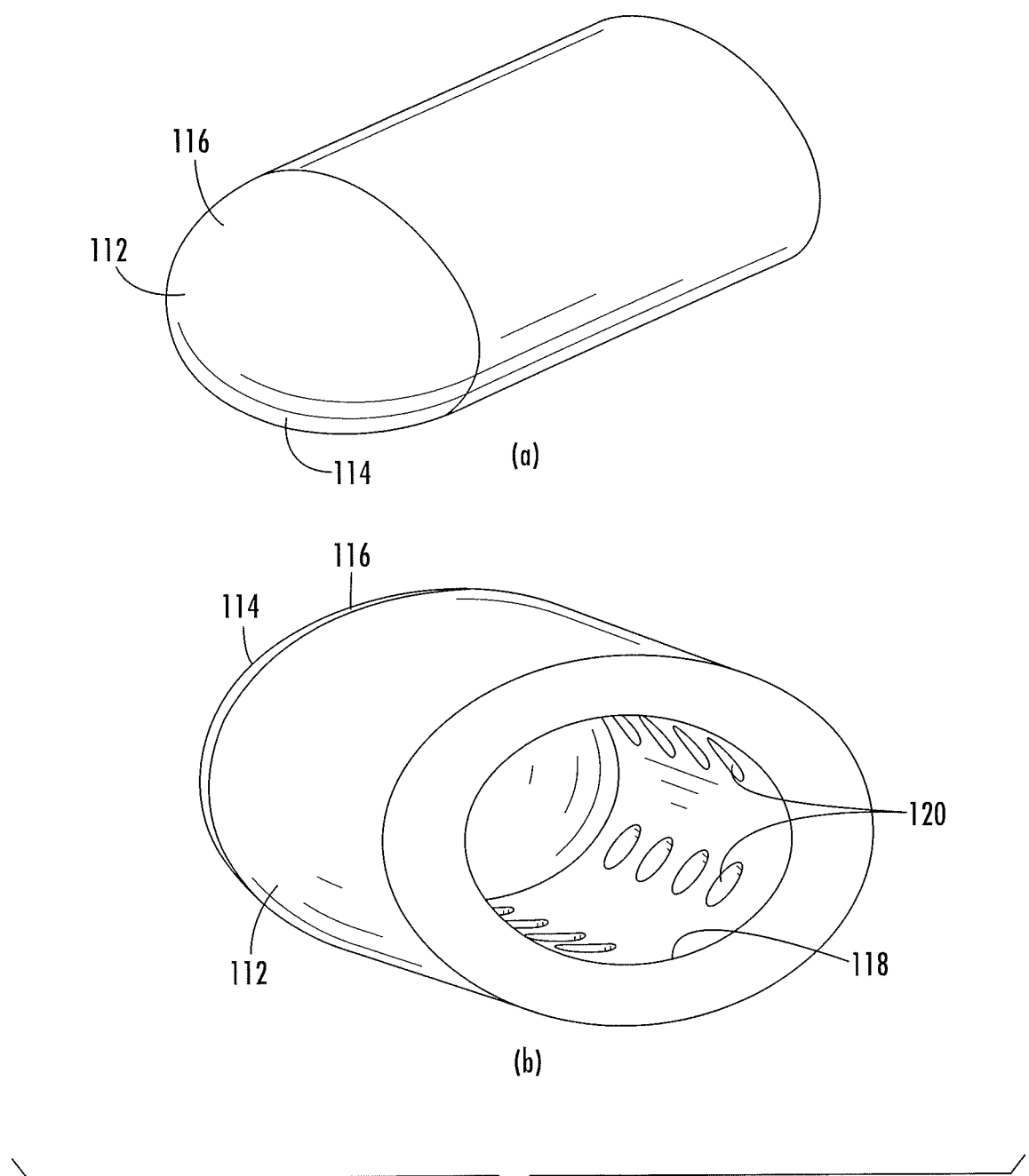
FIG. 16a is a perspective view of another embodiment of an end portion of the cleaning tool of FIG. 1, the end portion having a bullet shape.
FIG. 16b is a perspective view of the end portion of FIG. 16a showing an inner surface of the end portion.

Referring to FIGS. 16a and 16b, shown therein is another embodiment of an end portion 112 for a cleaning tool similar to the cleaning tool 10. The end portion 112 has a bullet shaped tip 114, such as a cylinder with a domed end 116 and a single opening 118 that would be lined with plastic bristles or possibly another similar cleaning surface such as abrasive pads (not shown). In use, an operating surgeon would insert surgical tools into the opening 118 of the bullet shaped tip 114 and remove charred tissue from the tools via contact and friction with the abrasive surface. This design allows for the collection of charred tissue, the supply of liquid to the cavity via a plurality of ports 120 as shown in FIG. 16b, and to the adaption of being either a manual or a motorized tool. This system may be used in open robotic procedures such as transoral robotic surgery. The handle may be malleable and the shape changed by the assistant at the bedside to allow the end portion to reach the surgeons cautery/laser tool.

Referring to FIGS. 19a-19d, the end portion 112 may be attached to a shaft 121 by hinges 123 so that the end portion 112 may be rotated 180°. The end portion 112 may also be fixed to the shaft 121 by a ring 127 at various angled degrees. In another embodiment, the end portion 112 may be connected to the shaft 121 with gears 125 for angling the end portion 112. The end portion 112 would be rotatable mechanically via the gears 125 operationally connected to a trigger on the handle of a cleaning tool as described herein. Movement of the gears 125 may be motorized.

Figure 17:
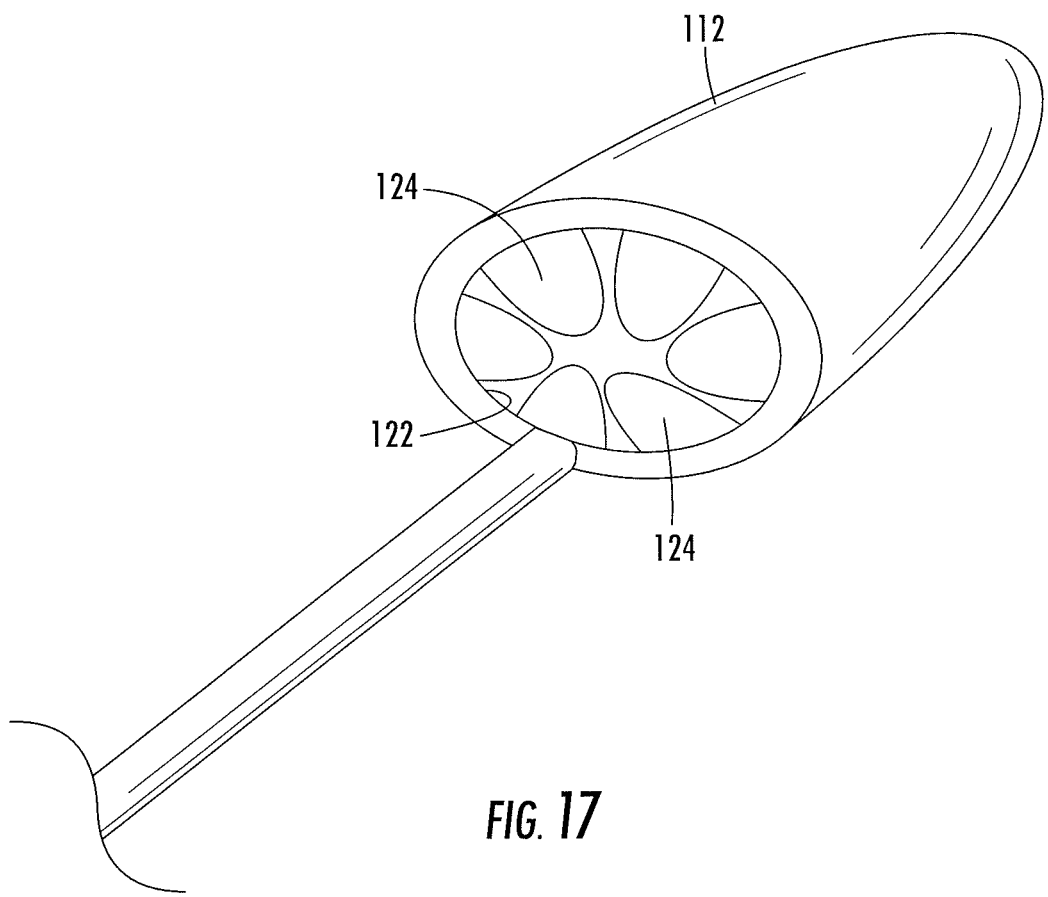
FIG. 17 is another embodiment of the end portion of FIG. 16a showing an inner cavity having flaps.

In another embodiment, an inner cavity 122 of the end portion 112 includes a plurality of flaps 124 for collecting charred tissue once it has been removed from a surgical tool tip, such as a cautery tool (FIG. 17). The plurality of flaps 124 may be constructed of rubber, plastic and the like. The flaps 124 allow the surgical tool to be inserted into the end portion 112 and to scrap the char from the tool as it is removed from the end portion 112.

Figure 18:
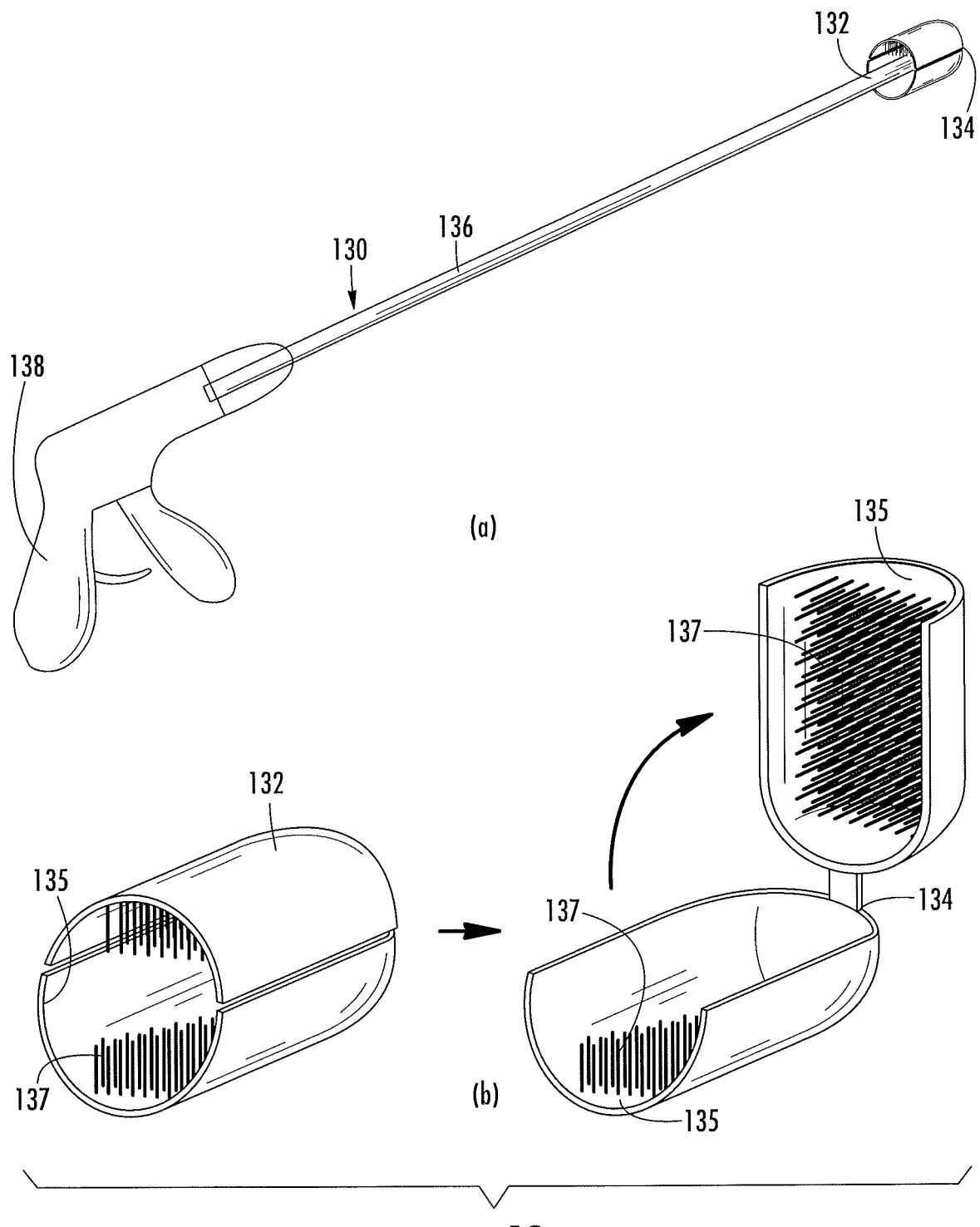
FIGS. 18a-18b are perspective views of another embodiment of a cleaning tool having an end portion having a hinge.
Figure 19:
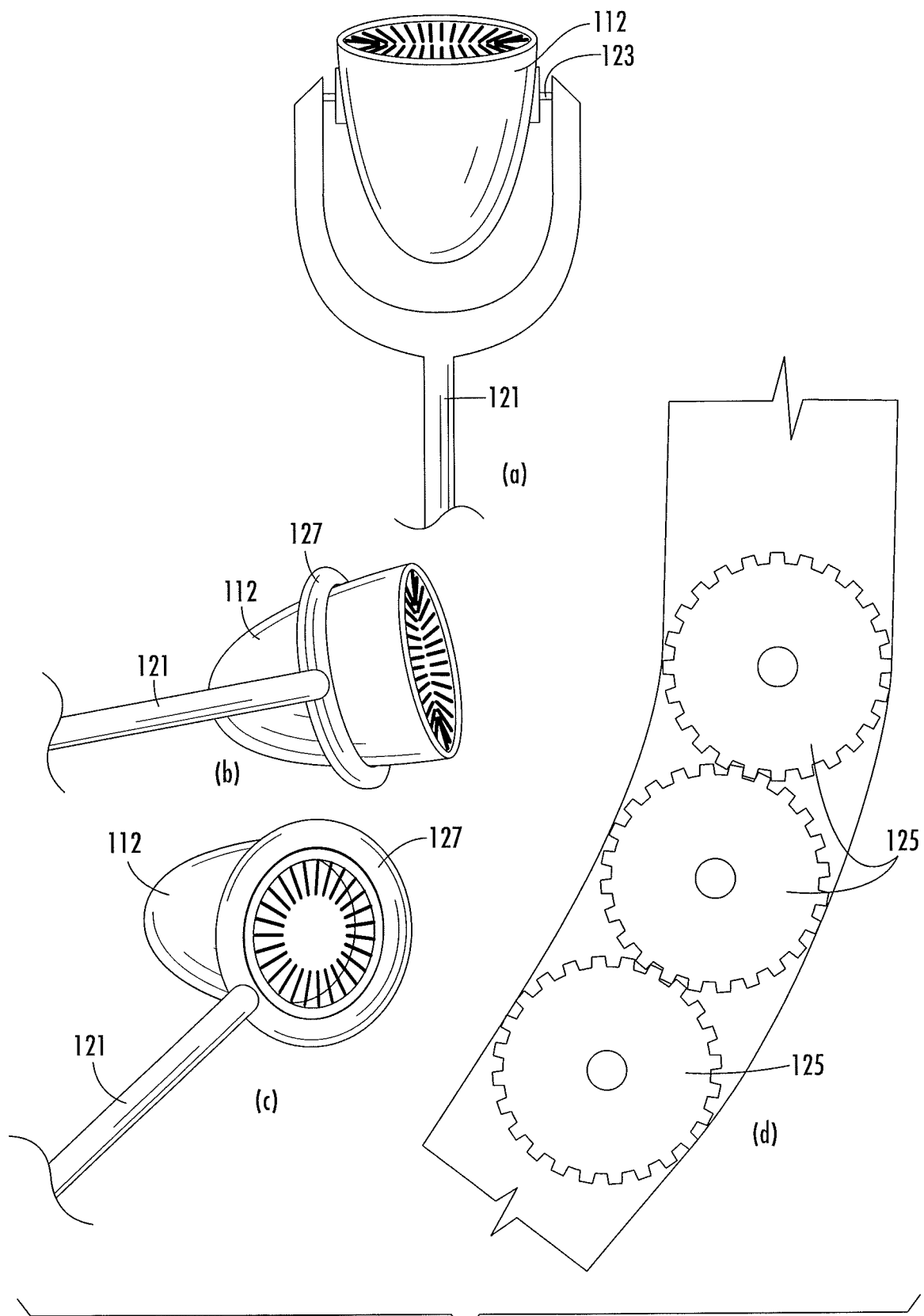
FIGS. 19a-19d are perspective views of another embodiment of an end portion of FIG. 16a with various methods of attaching the end portion to a shaft of the cleaning tool.

Referring to FIGS. 18a and 18b, another embodiment of a cleaning tool 130 similar to the cleaning tool 110 is shown herein except that an end portion 132 at the end of a shaft 136 is split in half along a hinge 134. The hinge 134 allows the end portion 132 to be opened wider for receiving a surgical tool, as opposed to having a single point of entry. The hinge 134 is controlled via a trigger mechanism of a laparoscopic tool handle 138 as disclosed herein. An inner surface 135 of the end portion 132 includes a plurality of cleaning elements 137 for cleaning off a surgical tool.

Figure 20:
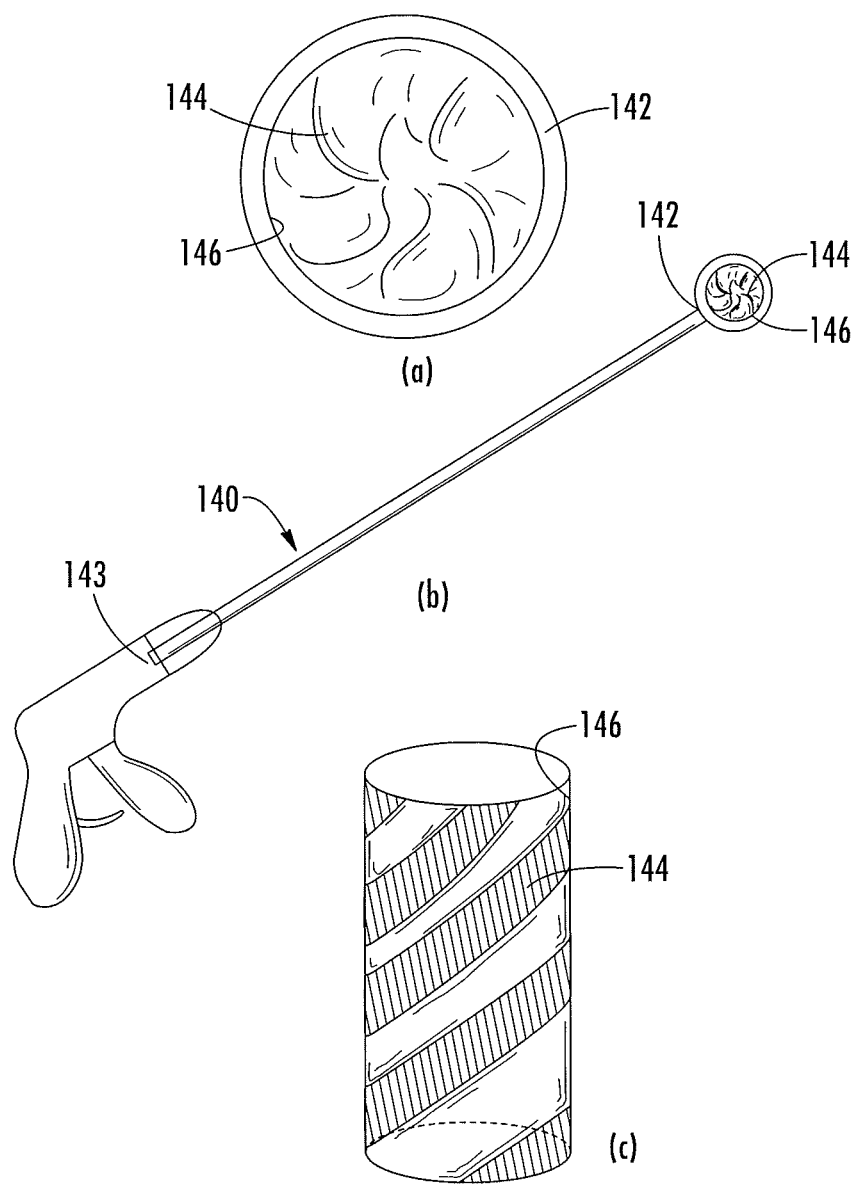
FIGS. 20a-20c are side views of another embodiment of a cleaning tool having a rotatable end portion.

Referring to FIGS. 20a-20c, shown therein is another embodiment of a cleaning tool 140 similar to cleaning tool 110 except that an end portion 142 having a bullet shaped tip rotates based on the input of a trigger mechanism on a laparoscopic tool 143 as described herein. A series of strips of a cleaning material 144 are provided on an interior portion 146 of the end portion 142 for cleaning a surgical tool. Alternatively, the interior portion 146 of the end portion 142 could be lined with alternating strips of abrasive pads or bristles and a softer sponge-like material that could hold a lubricant or a coolant. In another embodiment, the cleaning element comprises an absorbent material which may be soft or fluffy so as to retain liquid, resist high temperatures, and be able to clean charred tissue off of cautery tools.

Figure 21:
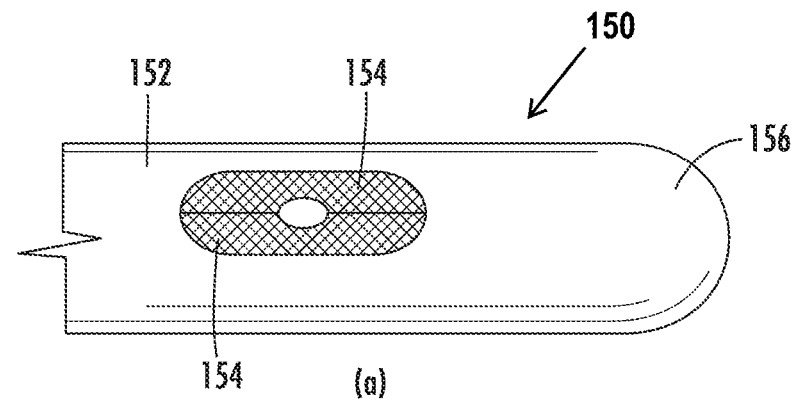
FIGS. 21a-21b are side views of another embodiment of an end portion of FIG. 16a, the end portion having a rod with a plurality of entry points.
Figure 21:
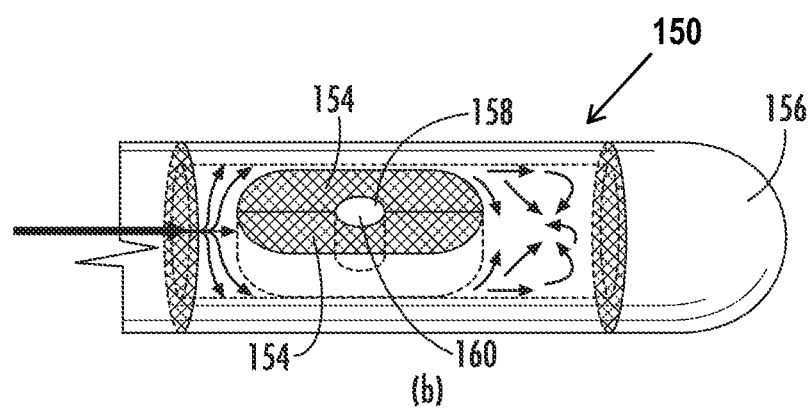

Referring to FIGS. 21a and 21b, shown therein is another embodiment of a portion of a cleaning tool 150 similar to the cleaning tool 10 except that the cleaning tool 150 includes a rod 152 (end effector) with a plurality of entry points 154 for the cautery tools near a tip 156 of the cleaning tool 150. Inside of the plurality of entry points 154, sponges 158 are used as the cleaning element to remove the charred tissue from the cautery tools. An opening 158 in the sponge 160, as well as splitting the sponge into two segments, allows easy entry for the cautery tools as well as cleaning surface to remove tissue. A liquid cooling system is provided to the cleaning tool 150 in which water or saline could be supplied to the sponges 158 through the rod 152.

Figure 22:
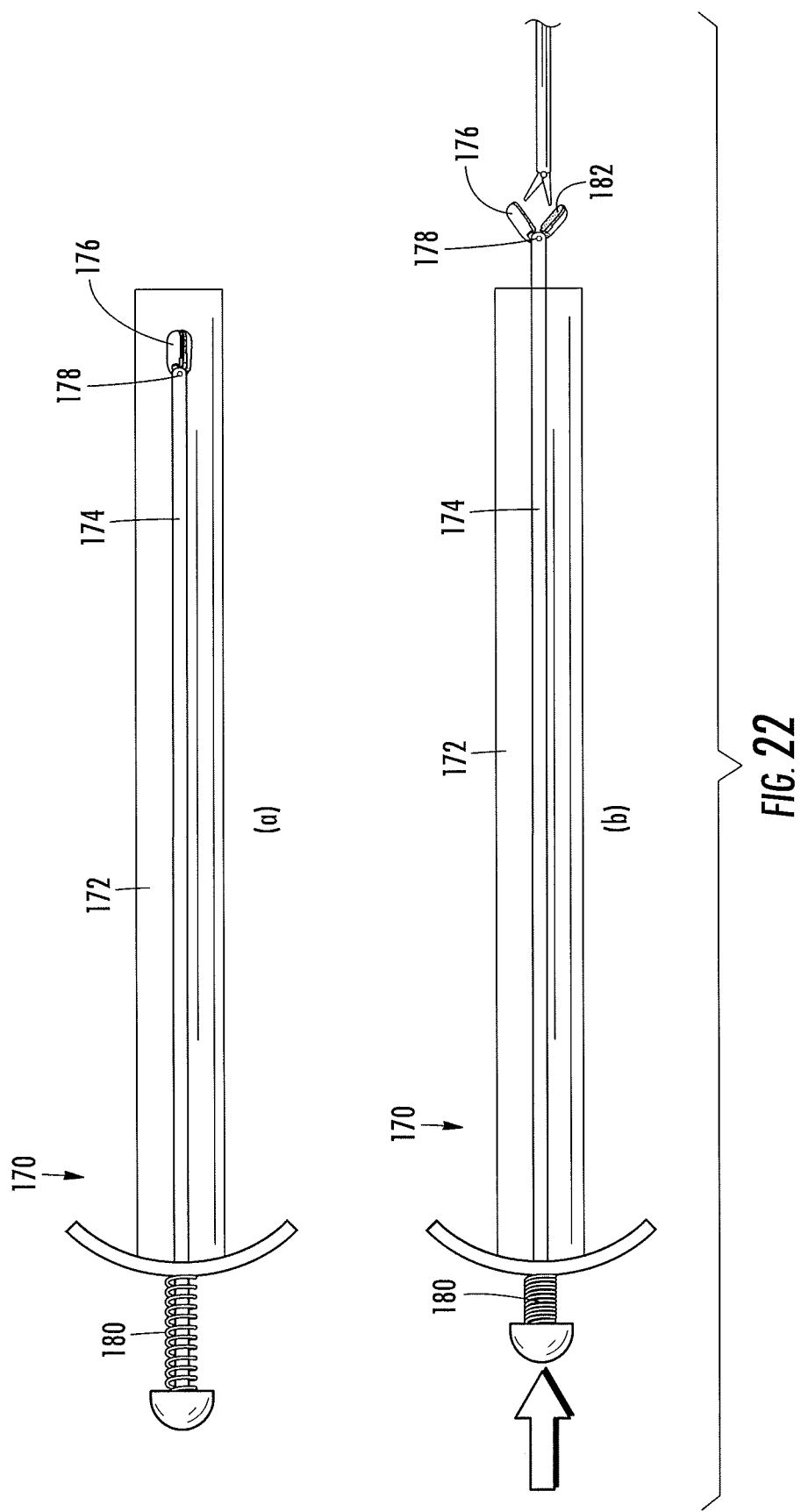
FIG. 22a is a side view of another embodiment of cleaning tool having an end portion in a retracted position.
FIG. 22b is a side view of the cleaning tool of FIG. 22a having an end portion in an expanded position.

Referring now to FIGS. 22a and 22b, shown therein is another embodiment of a cleaning tool 170 similar to the cleaning tool 10 except that the cleaning tool 170 comprises a hollow, cylindrical shaft 172 which contains an inner cylindrical shaft 174 with metal tongs 176 at its end 178 that are shaped like claws. The cleaning tool 170 is movable between a retracted position (FIG. 22a) and an expanded position (FIG. 22b). In the retracted position, the shaft 174 is compressed into the external hollow cylindrical shaft 172 by means of a spring 180. In the expanded position, the tongs 176 extend out of the cylinder and expand. The tongs 176 of the cleaning tool 170 have cleaning elements 182 (e.g., bristles, foam pads, or other abrasive pads) attached thereto. In use, a surgeon maneuvers his surgical tool to the middle of the tongs 176 in an open position. The assistant then causes the tongs 176 to be retracted wherein they collapse upon the surgical tool producing friction on the surgical tool so as to remove the charred tissue.

While the presently disclosed inventive concepts have been described herein in connection with certain embodiments so that aspects thereof may be more fully understood and appreciated, it is not intended that the presently disclosed inventive concepts be limited to these particular embodiments. On the contrary, it is intended that all alternatives, modifications and equivalents are included within the scope of the presently disclosed inventive concepts as defined herein. Thus the examples described above, which include particular embodiments, will serve to illustrate the practice of the presently disclosed inventive concepts, it being understood that the particulars shown are by way of example and for purposes of illustrative discussion of particular embodiments of the presently disclosed inventive concepts only and are presented in the cause of providing what is believed to be the most useful and readily understood description of procedures as well as of the principles and conceptual aspects of the inventive concepts. Changes may be made in the formulation of the various compositions described herein, the methods described herein or in the steps or the sequence of steps of the methods described herein without departing from the spirit and scope of the presently disclosed inventive concepts.

What is claimed is:

1. A surgical cleaning tool, comprising:
a shaft having a distal end and a proximal end;
a handle attached to the distal end of the shaft;
an end portion connected to the proximal end of the shaft, wherein the end portion has an outer surface, an inner cavity, an inner surface, at least one cleaning element connected to at least a portion of the inner surface, and an opening in a wall portion of the end portion, wherein the opening is along the length of the wall portion and wherein the opening allows access through the wall portion to the at least one cleaning element in the inner cavity of the end portion;
a hinge mechanism positioned between the end portion and the proximal end of the shaft; and
a trigger mechanism in the handle, wherein the trigger mechanism enables actuation of movement of the hinge mechanism by a user to effect a change in an angle of the end portion in relation to the shaft;
and wherein the cleaning tool is independent of a surgical instrument.

2. The surgical cleaning tool of claim 1, further comprising a conduit for supplying a cooling solution to the at least one cleaning element during use.

3. The surgical cleaning tool of claim 1, wherein the shaft and end portion each has an external diameter which is sized to be able to allow insertion into a laparoscopic surgical port of a patient undergoing a surgical procedure.

4. The surgical cleaning tool of claim 1 wherein a portion of the shaft is hollow for receiving a conduit for supplying a cooling solution to the at least one cleaning element.

5. A method of cleaning a surgical tool, comprising:
providing a cleaning tool, the cleaning tool comprising:
a shaft having a distal end and a proximal end;
a handle attached to the distal end of the shaft; and
an end portion connected to the proximal end of the shaft, wherein the end portion has an outer surface, an inner cavity, an inner surface, at least one cleaning element connected to at least a portion of the inner surface, and an opening in a wall portion of the end portion, wherein the opening is along the length of the wall portion and wherein the opening allows access through the wall portion to the at least one cleaning element in the inner cavity of the end portion;
positioning at least the end portion of the cleaning tool within a body cavity of a patient undergoing a surgical procedure; and
causing a surgical tool in the body cavity to engage the end portion of the cleaning tool, wherein at least a portion of the surgical tool is inserted into the opening of the end portion of the cleaning tool, and wherein the surgical tool is rubbed and/or scraped against the at least one cleaning element of the end portion of the cleaning tool to remove charred tissue from the surgical tool while the surgical tool is within the body cavity; and wherein the cleaning tool is independent of the surgical tool.

6. The method of claim 5, wherein the cleaning tool further comprises a hinge mechanism positioned between the end portion and the proximate end of the shaft, and a trigger mechanism in the handle, wherein the trigger mechanism enables actuation of movement of the hinge mechanism by a user to effect a change in an angle of the end portion in relation to the shaft.

7. The method of claim 5, wherein the cleaning tool further comprises a conduit for supplying a cooling solution to the at least one cleaning element during use.

8. The method of claim 7, wherein a portion of the shaft of the cleaning tool is hollow for receiving the conduit.

9. The method of claim 5, wherein the shaft and end portion of the cleaning tool each has an external diameter which is sized to be able to allow insertion into a laparoscopic surgical port of a patient undergoing a surgical procedure.

10. A method of cleaning a surgical tool, comprising:
providing a cleaning tool, the cleaning tool comprising:
a shaft having a distal end and a proximal end;
a handle attached to the distal end of the shaft;
an end portion connected to the proximal end of the shaft, wherein the end portion has an outer surface, an inner cavity, an inner surface, at least one cleaning element connected to at least a portion of the inner surface, and an opening in a wall portion of the end portion, wherein the opening allows access to the at least one cleaning element in the inner cavity of the end portion; and
a conduit for providing a cooling solution to the at least one cleaning element during use;
positioning at least the end portion of the cleaning tool within a body cavity of a patient undergoing a surgical procedure;
causing a surgical tool in the body cavity to engage the end portion of the cleaning tool, wherein at least a portion of the surgical tool is inserted into the opening of the end portion of the cleaning tool, and wherein the surgical tool is rubbed and/or scraped against the at least one cleaning element of the end portion of the cleaning tool to remove charred tissue from the surgical tool while the surgical tool is within the body cavity, and wherein the cleaning tool is independent of the surgical tool; and
providing the cooling solution via the conduit to the at least one cleaning element.

11. The method of claim 10, wherein the cleaning tool further comprises a hinge mechanism positioned between the end portion and the proximate end of the shaft, and a trigger mechanism in the handle, wherein the trigger mechanism enables actuation of movement of the hinge mechanism by a user to effect a change in an angle of the end portion in relation to the shaft.

12. The method of claim 10, wherein a portion of the shaft of the cleaning tool is hollow for receiving the conduit.

13. The method of claim 10, wherein the shaft and end portion of the cleaning tool each has an external diameter which is sized to be able to allow insertion into a laparoscopic surgical port of a patient undergoing a surgical procedure.

* * * * *